(12) United States Patent
Wong

(10) Patent No.: US 7,329,870 B2
(45) Date of Patent: Feb. 12, 2008

(54) SIMPLE MULTI-CHANNEL NDIR GAS SENSORS

(75) Inventor: Jacob Y. Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 2 days.

(21) Appl. No.: 11/198,106

(22) Filed: Aug. 5, 2005

(65) Prior Publication Data

US 2007/0029488 A1    Feb. 8, 2007

(51) Int. Cl.
*G01J 5/02* (2006.01)
(52) U.S. Cl. .................................. 250/341.1
(58) Field of Classification Search ............. 250/341.1
See application file for complete search history.

(56) References Cited

U.S. PATENT DOCUMENTS

| 4,914,719 A | * | 4/1990 | Conlon et al. | ......... 250/339.13 |
| 5,026,992 A | * | 6/1991 | Wong | ......................... 250/343 |
| 7,132,658 B2 | * | 11/2006 | Weckstrom et al. | ... 250/339.13 |

FOREIGN PATENT DOCUMENTS

| WO | WO 2007029487 A1 | * | 3/2007 |
| WO | WO 2007064370 A2 | * | 6/2007 |

* cited by examiner

Primary Examiner—David Porta
Assistant Examiner—David S Baker
(74) Attorney, Agent, or Firm—Wagner, Anderson & Bright, LLP; Roy L. Anderson

(57) ABSTRACT

Concentrations of N gas species can be detected from a single beam NDIR gas sensor having a differential infrared source and an (N+1)-passband filter (having a neutral passband and N absorption passbands for N gases) mounted at a single infrared detector by driving the infrared source with N input power levels to render the source into emitting at N distinct temperatures whose radiation outputs are characterized by N corresponding Planck curves which are dependent only upon the respective source temperatures and which link a Spectral Radiant Emittance MsubLamba with wavelength, measuring N detector outputs at the single infrared detector and detecting the concentrations of N different gas species, each of the N gas species having its own unique infrared absorption passband, by (a) setting up N causality relationship equations linking outputs of the detector respectively for N different source temperatures and a set of relevant parameters of the sensor components, (b) determining the values of all of the parameters for the N equations utilizing appropriate boundary conditions except the N concentrations for the respective N gas species, and (c) solving for the N gas concentrations with the measured N detector outputs, there being N equations and N unknowns, when N is an integer of 2 or more.

11 Claims, 2 Drawing Sheets

Three blackbody Planck curves depicting respectively infrared source temperatures of T1 = 900°K, T2 = 700°K and T3 = 500°K. Also shown are the Center Wavelengths (CWL's) of absorption bands for gases G1, G2, G3 and the neutral reference gas GN.

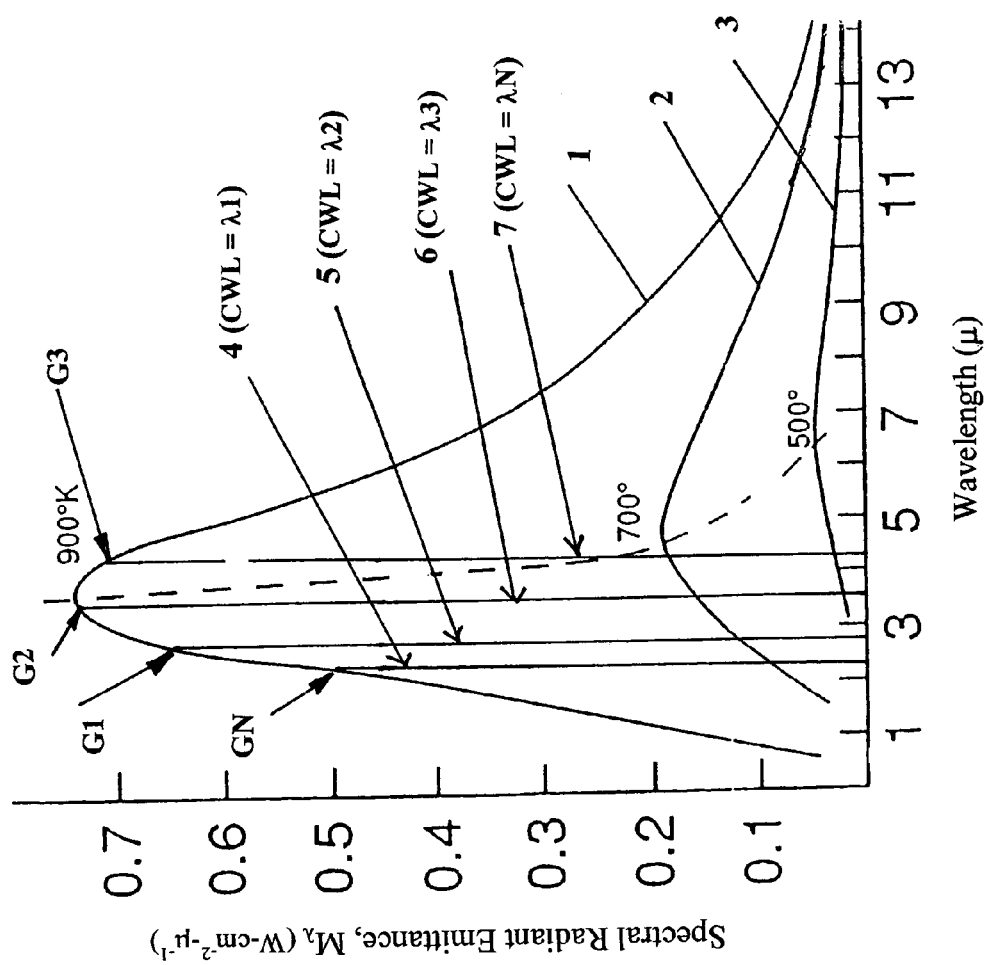
Figure 1. Three blackbody Planck curves depicting respectively infrared source temperatures of T1 = 900°K, T2 = 700°K and T3 = 500°K. Also shown are the Center Wavelengths (CWL's) of absorption bands for gases G1, G2, G3 and the neutral reference gas GN.

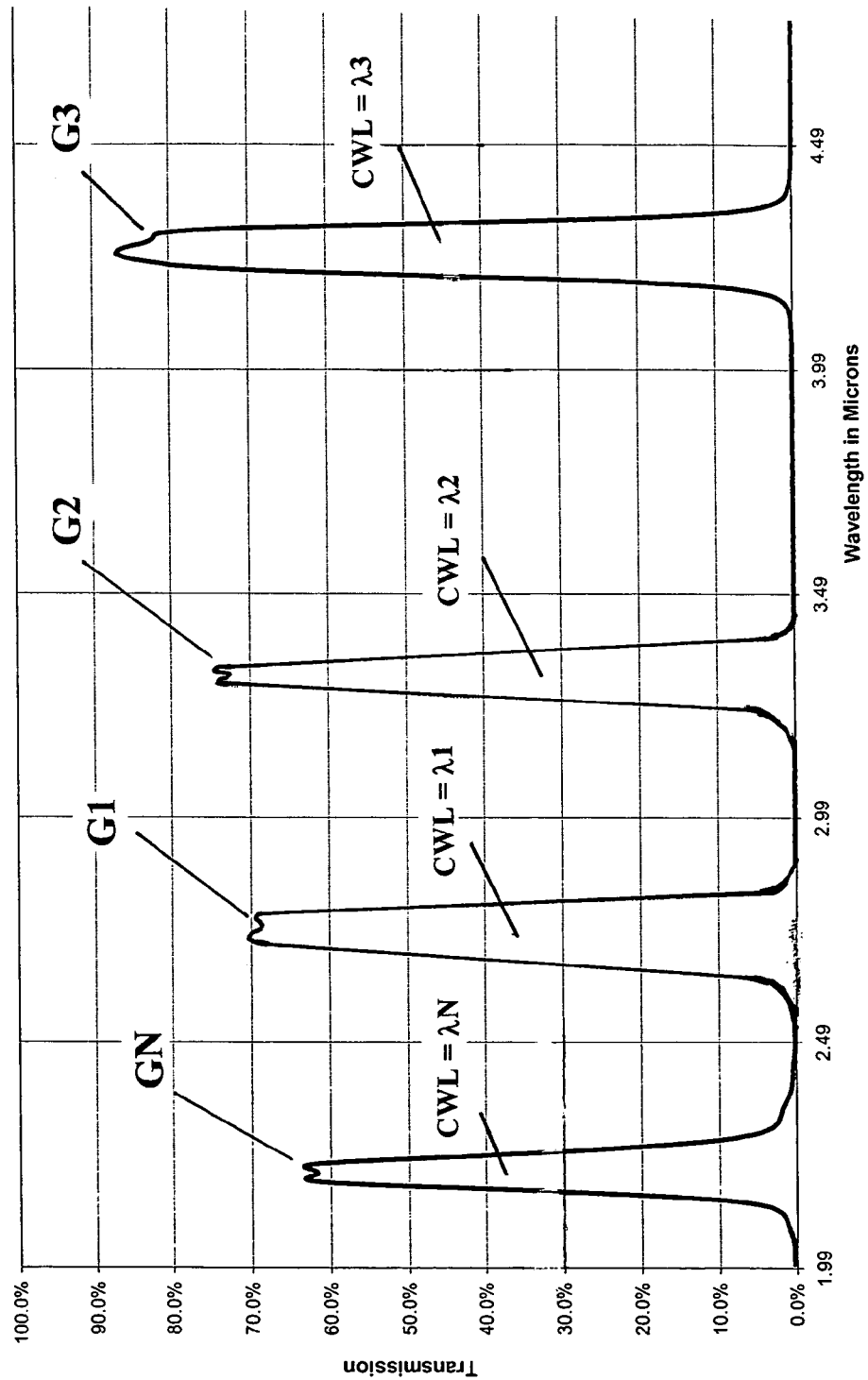
Figure 2. The transmittance curve for the custom 4-passband interference filter depicting the four respective Center Wavelengths (CWL's) of the absorption bands for the gases G1, G2, G3 and the neutral reference.

SIMPLE MULTI-CHANNEL NDIR GAS SENSORS

CROSS-REFERENCE TO RELATED APPLICATIONS

The present application is related to U.S. Ser. No. 11/197,790, filed Aug. 4, 2005, the disclosure of which is specifically incorporated herein by reference.

FIELD OF THE INVENTION

The present invention generally relates to the field of gas sensing devices and, more particularly, to NDIR gas analyzers.

BACKGROUND OF THE INVENTION

Non-Dispersive infrared (NDIR) gas analyzers have been used for detecting the presence and concentration of various gases for over four decades. The NDIR technique has long been considered as one of the best methods for gas measurement. In addition to being highly specific, NDIR gas analyzers are also very sensitive, stable and easy to operate and maintain.

In contrast to NDIR gas sensors, the majority of other types of gas sensors today are in principle interactive. Interactive gas sensors are less reliable, generally nonspecific, and in some cases can be poisoned or saturated into a nonfunctional or irrecoverable state.

Despite the fact that interactive gas sensors are mostly unreliable and that the NDIR gas measurement technique is one the of best there is, NDIR gas analyzers have still not enjoyed widespread usage to date mainly because of the fact that their cost is still not low enough as compared to other inferior gas sensors for many applications.

In the past, NDIR gas analyzers typically included an infrared source, a motor-driven mechanical chopper to modulate the source, a pump to push or pull gas through a sample chamber, a narrow bandpass interference filter, a sensitive infrared detector plus expensive infrared optics and windows to focus the infrared energy from the source to the detector. In an attempt to reduce the cost and simplify the implementation of the NDIR methodology, a low-cost NDIR gas sensor technique was earlier developed. This low-cost NDIR technique employs a diffusion-type gas sample chamber of the type disclosed in U.S. Pat. No. 5,163,332, issued on Nov. 17, 1992 to Wong, the present applicant. This diffusion-type gas sample chamber eliminates the need for expensive optics, mechanical choppers and a pump for pushing or pulling the gas into the sample chamber. As a result, a number of applications using NDIR gas sampling technique, which were previously considered impractical because of cost and complexity, have been rendered viable ever since.

In the ensuing years since U.S. Pat. No. 5,163,332 was issued, Wong, the present applicant, has continued to refine and improve low-cost NDIR gas sampling techniques as evidenced by the issuance of U.S. Pat. No. 5,222,389 (June 1993), U.S. Pat. No. 5,341,214 (August 1994), U.S. Pat. No. 5,347,474 (September 1994), U.S. Pat. No. 5,453,621 (September 1995), U.S. Pat. No. 5,502,308 (March 1996), U.S. Pat. No. 5,747,808 (May 1998), U.S. Pat. No. 5,834,777 (November 1998) and U.S. Pat. No. 6,237,575 (May 2001) to same. Until recently, efforts to reduce the cost of an NDIR gas sensor have been concentrated mainly in the areas of developing lower cost infrared components, improving sensor structural and optical designs and forging innovations and simplifications in electronic signal processing circuits. Hardly any significant effort has been devoted to sensor cost reduction via new NDIR sensor methodology.

Up until now, the most prevalent NDIR gas sensor today is a dual beam device having a signal and a reference beam implemented with a single infrared source and two separate infrared detectors, each having a different interference filter. The signal filter contains a narrow spectral passband that allows radiation relevant to the absorption of the gas to be detected to pass. Thus the presence of the gas of interest will modulate the signal beam. The reference filter contains a narrow spectral passband that is irrelevant to the gas in question and also to all the common gases present in the atmosphere. Therefore the reference beam will stay constant and act as a reference for the detection of the designed gas species over time. Although the dual beam technique works well for a host of applications, especially with the detection of relatively low concentration of Carbon Dioxide ($CO_2$) gas (400-2,000 ppm) for HVAC (Heating, Ventilation and Air Conditioning) and IAQ (Indoor Air Quality) applications, the cost of the sensor is limited by the expensive detector package which contains two detectors each equipped with a different interference filter. Furthermore, the dual beam NDIR gas sensor still has a number of shortcomings that require special treatments in order to render the sensor adequately reliable and stable for use over time. These shortcomings include the aging of the infrared source which might cause the spatial distribution of infrared radiation reaching the detectors to change; the same applies to the non-uniform aging of the inner reflective surfaces of the sample chamber affecting the spatial distribution of the impinging radiation at the detector assembly, the different aging characteristics for the two interference filters each being manufactured via different deposition processing steps and optical materials and finally the potential different aging characteristics for the two detectors.

Logic would dictate that in order to improve the performance and to lower the cost of the ever more popular dual beam NDIR gas sensor, one has to resort to system structural or optical simplification and/or system components reduction. Taking the case of the dual beam NDIR gas sensor as an example, there are two ways that one can accomplish these objectives. First, one can reduce the number of detectors from two to one which automatically implies that the number of interference filters would also be reduced from two to one. In other words, one can attempt to convert the dual beam sensor methodology to a single beam one. Alternatively, one can increase the measurement capability of the dual beam sensor from being able to detect just one gas into one that can simultaneously detect two or more gases. If either of these two cases is successful, it would be equivalent to being able to reduce the unit cost for the dual beam NDIR sensors.

It is of interest to note that back in 1991 and prior to the issuance of U.S. Pat. No. 5,163,332 (1992) to Wong for the advent of the so-called "waveguide sample chamber," the same inventor has earlier advanced the concept of a single beam NDIR sensor methodology using a spectral ratioing technique with a differential temperature source in U.S. Pat. No. 5,026,992 (1991). After almost 15 years, this concept has to date neither been proven to be viable in theory nor has it been experimentally demonstrated in order to illustrate its practicality. It was found out only very recently by Wong, the current applicant and the original author of U.S. Pat. No. 5,026,992 (1991), that although the concept advanced in said patent was sound, the method did not work when the prescribed steps were followed exactly according to the teaching of the patent. In a companion patent application entitled "Ultra Low Cost NDIR Gas Sensors" and co-authored with C. W. Tse, filed Aug. __, 2005 with Attorney Docket No. 35.121, the disclosure of which is specifically incorporated herein by reference, the authors reported their experimental results in proving definitively the impracticality of implementing such a single beam NDIR sensor using differential source temperature technique as advanced in U.S. Pat. No. 5,026,992 (1991). The authors went on to advance a novel real time programmable infrared source control method which makes the single beam NDIR sensor concept as disclosed in U.S. Pat. No. 5,026,992 (1991) experimentally viable in practice. Furthermore, the same authors advance in the same disclosure a new single beam NDIR sensor methodology which can work with a non-genuine blackbody source such as a low cost miniature incandescent light bulb in lieu of an expensive genuine blackbody source as stipulated in U.S. Pat. No. 5,026,992 (1991).

There is still a long felt need in many industries and applications to use still lower cost NDIR gas sensors. It is this need that drives the current applicant to continue to develop new and novel sensor techniques in order to bring about NDIR gas sensors with the lowest possible costs. Based upon the latest experimental results the current applicant obtained very recently about U.S. Pat. No. 5,026,992 and additional related research and development work he has carried out, the concept disclosed in the referred to patent was revisited and has now been advanced into a new and experimentally valid framework such that a single beam NDIR gas sensor can actually be used, for the first time, to simultaneously detect two or more gas species in accordance with the teachings of this present application.

SUMMARY OF THE INVENTION

The present invention is generally directed to a method for detecting the concentrations of N gas species from a single beam NDIR gas sensor having a differential infrared source and an (N+1)—passband filter (having a neutral passband and N absorption passbands for N gases) mounted at a single infrared detector by driving the infrared source with N input power levels to render the source into emitting at N distinct temperatures whose radiation outputs are characterized by N corresponding Planck curves which are dependent only upon the respective source temperatures and which link a Spectral Radiant Emittance MsubLamba with wavelength, measuring N detector outputs at the single infrared detector and detecting the concentrations of N different gas species, each of the N gas species having its own unique infrared absorption passband, by (a) setting up N causality relationship equations linking outputs of the detector respectively for N different source temperatures and a set of relevant parameters of the sensor components, (b) determining the values of all of the parameters for the N equations utilizing appropriate boundary conditions except the N concentrations for the respective N gas species, and (c) solving for the N gas concentrations with the measured N detector outputs, there being N equations and N unknowns, when N is an integer of 2 or more.

In a first, separate group of aspects of the present invention, a single beam NDIR gas sensor for detecting the concentrations of N gas species according to the method of the present invention is disclosed which includes a differential infrared source (which may be a genuine or a non-genuine blackbody source), a single infrared detector, a multiple-passband filter mounted at the single infrared detector having a neutral passband and N absorption passbands for N gases species incorporated into the multiple-passband filter, each of the N gas species having its own unique infrared absorption passband, a driver for the infrared source with N input power levels so as to render said source into emitting at N distinct temperatures whose radiation outputs are characterized by N corresponding Planck curves which are dependent only upon the respective source temperatures and which link a Spectral Radiant Emittance MsubLamba with wavelength, and electronics for detecting the concentrations of N different gas species by solving N causality relationship equations with N unknowns linking outputs of the detector respectively for N different source temperatures and a set of relevant parameters of the sensor components that have been determined utilizing appropriate boundary conditions except the N concentrations for the respective N gas species, wherein N is an integer of 2 or more.

In other, separate aspects of the present invention, each of the N absorption passbands for N gases is specific to passing a particular spectral radiation for one of the N gases to be detected, the values of all of the parameters of the N causality relationship equations except for the N concentrations for the respective N gas species are performed as part of an initialization process and then the N concentrations can be carried out repeatedly as part of a real time process to detect the concentrations of N different gas species through use of N calibration curves.

Accordingly, it is a primary object of the present invention to develop a new and novel sensor concept for the realization of the long sought after ultra low cost NDIR gas sensors.

This and further objects and advantages will be apparent to those skilled in the art in connection with the drawings and the detailed description of the preferred embodiment set forth below.

BRIEF DESCRIPTION OF THE DRAWINGS

FIG. 1. Three blackbody Planck curves depicting respectively infrared source temperatures of T1=900° K, T2=700° K and T3=500° K. Also shown are the Center Wavelengths (CWL's) of absorption bands for gases G1, G2, G3 and the neutral reference gas GN.

FIG. 2. The transmittance curve for the custom 4-passband interference filter depicting the four respective Center Wavelengths (CWL's) of the absorption bands for the gases G1, G2, G3 and the neutral reference.

DETAILED DESCRIPTION OF THE INVENTION

As noted in the Background of the Invention above, the single beam NDIR gas sensor technique using a differential source temperature ratioing concept as advanced in U.S. Pat. No. 5,026,992 (1991) can be rendered practically viable when additional new and novel ideas are incorporated into same. Furthermore, it was proven that a non-genuine blackbody source, such as a low cost miniature incandescent light bulb, in lieu of a more costly genuine blackbody, could be employed to render the concept workable. However, the concept disclosed in said patent only works for a single beam NDIR sensor detecting just one gas species. In view of the latest experimental findings in an accompanying patent application entitled "Ultra Low cost NDIR Gas Sensors" by Wong and Tse, it is the object of the current invention to reformulate this concept anew from a one-channel application or a single gas detection, to a multi-channel application for simultaneously detecting two or more gases, while still remaining as a single beam NDIR gas sensor.

In order to accomplish a single beam NDIR gas sensor capable of simultaneously detecting two or more gases, a new mathematical model based upon a new conceptual framework covering the analytical procedures for achieving said results has to be developed anew. The thinking of this conceptual framework is distinctly different from the ad hoc approach taken in U.S. Pat. No. 5,026,992 (1991) for exploiting the fact that by operating a genuine blackbody source at two different input power levels, one is capable of shifting the spectral content of the source in two distinct ways according to the well-known Planck's Law of radiation. The current invention takes a much broader view in realizing that by operating the infrared source at N distinct power levels, it is equivalent to having N+1 detectors each equipped with a unique bandpass filter of its own. With the exception of one single detector among the N+1 ones, which is equipped with a reference or neutral filter, namely radiation that passes such a filter is irrelevant to the N gas species of interest for detection and also to all common gases that are present in the atmosphere, each of the N remaining detectors has a unique bandpass filter of its own for detecting a specific gas species. Such an equivalence is elegantly expressed as a set of simultaneous equations encompassing all the characteristic parameters for the blackbody source, the single infrared detector, the (N+1)-passband filter and last but not least, all the absorption properties of the gases to be detected. In order to be able to quantitatively formulate such a mathematical model, one must have a full comprehension of the physics of NDIR gas detection and all the relevant gas laws that govern the behavior of all the pertinent gases to be detected.

The logistical thinking for the currently invented functional formulation for a single beam NDIR gas sensor capable of detecting N gas species can be briefly summarized as follows. First, the interference filter equipped at the single detector must have N+1 passbands each of which is specific to passing a particular spectral radiation. As alluded to earlier, N is also the number of input power levels used to drive the source creating in effect N distinct emitting blackbody temperatures for the source. Second, among the N+1 passbands, one is designated as the reference or neutral and it passes radiation that is irrelevant to the N gas species to be detected and also to all the common gas species that are present in the atmosphere. Third, each of the remaining N passbands passes the radiation that is relevant to or will be absorbed by one specific gas species to be detected. Fourth, for the detection of N gas species by the single beam NDIR gas detector, there will be N distinct input power levels sequentially driving the blackbody source (genuine or nongenuine type). Fifth, for each of the N input power levels driving the source, a causality relationship is set up linking the output of the detector with the other pertinent parameters including the presence or absence of the gases to be detected and their respective concentration levels. Sixth, once the N such equations are set up, system phenomenological conditions are defined in such a way as to identify or permit the calculations of all the constant parameters appearing in the set of N equations. Finally, there remain only N unknowns in the set of N equations representing respectively the concentrations of the gas species to be detected. As such these N unknowns can be readily determined to yield the concentrations of the gas species that are present in the single beam gas chamber.

The advantage in a single beam NDIR sensor design and implementation using a differential source temperature concept so as to be able to simultaneously detect two or more gases is many-fold. First and foremost, having fewer infrared detectors is a simpler approach both from the sensor design and cost standpoints. The cost of N+1 detectors with N+1 interference filters is many times that of a single detector with just one (N+1)-passband filter. It is certainly true that present interference filter design and fabrication technologies might limit the value of the number N to less than 5. However, once technology permits, the cost of an N+1 passbands filter should not be much more expensive than a single passband filter. Thus, from the cost standpoint, a single beam NDIR gas sensor capable of detecting 2 or more gases simultaneously with just one filter could be very significant. Second, since there is in essence only one optical beam in this method design, one of the major disadvantages for the current widely used dual beam NDIR sensor, namely the non-uniform radiation distribution at the multi-detector assembly caused principally by the aging of sensor components, is virtually eliminated, and, for this reason the single beam NDIR gas sensor is inherently more reliable and stable over time. Third, because of the fact that there is only one infrared source and one infrared detector and the output signals are taken to be the ratio of the detector outputs for any two different source temperature emission states, everything common to the two temperature states, such as dirt in the windows or inside the sample chamber, aging for the detector and the source etc., are further minimized as compared to the traditional dual beam NDIR sensor.

The logistical thinking for the currently invented functional formulation will now be described in more detail. In theory, such a formulation can be generalized to any value of N where N is the number of gas species that can be simultaneously detected by the single beam NDIR sensor and N+1 is the number of passbands possessed by the single filter equipped at the single detector. For simplicity and efficacy of explanation, and without sacrificing any substance of the invention, we will arbitrarily set N=3. In other words, we will describe the formulation for a single beam NDIR detector capable of detecting simultaneously three different gas species using a custom interference filter having N+1=4 passbands at the detector. Since N is also the number of input power levels used to drive the source in order to produce three distinct blackbody temperatures, we will have in this case three individual Planck's curves for representing the three different spectral radiant emittances, $M_\lambda$'s, available from the source. FIG. 1 shows schematically three blackbody Planck curves (N=3) for the mathematical formulation of the present invention for a three-channel NDIR gas sensor, namely a sensor capable of simultaneously detecting the concentration of gases G1, G2 and G3 in the sample chamber. For a single beam NDIR sensor capable of detecting three gas species using the present invention, an "N+1=4"-passbands filter would have to be used.

FIG. 1 shows three blackbody Planck curves for temperatures at T1, T2 and T3 (in deg K), respectively. The blackbody Planck curve 1 is shown for source temperature T1=900° K or 627° C. The blackbody Planck curve 2 is shown for source temperature T2=700° K or 427° C. The blackbody Planck curve 3 is shown for source temperature T3=500° K or 227° C. Let the three gas species to be detected be G1, G2 and G3 with the respective CWL of their absorption bands, 4, 5 and 6 respectively located at $\lambda 1$, $\lambda 2$ and $\lambda 3$ as shown in FIG. 1. Also shown in FIG. 1 is the neutral reference band 7, located at $\lambda N$. The corresponding spectral transmittance characteristics for the custom 4-passband filter to be used in the current formulation are shown in FIG. 2. As alluded to earlier above, we have implicitly implied in the present formulation that a full comprehension of the physics and the state-of-the-art technology for NDIR gas detection, together with all the relevant gas laws governing the behavior of all pertinent gases to be detected, are assumed to be well understood. Such is illustrated for the four passbands depicted in FIG. 4 which have to be spectrally well separated from one another so as not to overstress the present technology limit for the design and fabrication of multi-passband filters.

Once we have defined the general framework for the current formulation as presented above, we are now ready to set up the causality relationship linking the outputs of the detector with the other pertinent sensor component parameters including the presence or absence of the gases to be detected and their respective concentrations. Let $M1(T)$, $M2(T)$ and $M3(T)$ be the spectral radiant emittances, $M_\lambda$ for the three optical channels respectively for gas species G1, G2 and G3 at blackbody temperature T. Similarly, let $MN(T)$ be the $M_\lambda$ for the reference optical channel at source temperature T. In other words, $M1(T)$ is the spectral radiant emittance, $M_\lambda$, of the blackbody source at temperature T impinging on the detector equipped with a custom spectral filter $F\lambda 1$ (having only the passband at CWL=$\lambda 1$). In this case the detector voltage signal output, $V_{M1,T}$, can be quantitatively expressed as follows:

$$V_{M1,T} = \in \times M1(T) \times \eta(\lambda 1) \times \Delta\lambda 1 \times \eta(OS) \times R \times G(COM) \text{ volts} \quad [1]$$

Where $V_{M1,T}$=Detector signal output for infrared source operating at temperature T for optical channel M1

$\in$=Blackbody source emissivity assumed to be independent of infrared source temperature T and $\lambda$ $M1(T)$=Spectral radiant emittance of blackbody source at T° K for filter $F\lambda 1$ $\eta(\lambda 1)$=Transmittance efficiency of filter $F\lambda 1$ at CWL $\Delta\lambda 1$=Full Width Half Maximum (FWHM) of filter $F\lambda 1$ $\eta(OS)$=Overall Optical System efficiency for single beam sensor R=Detector Responsivity (V/W) which is independent of $\lambda$ for thermopile detectors G(COM)=Common first stage amplifier gain for signal processing circuit, same for all three optical channels Since the blackbody Planck or $M_\lambda(T)$ curves are uniquely determined once the temperature of the blackbody source is known, one can establish the relationships between $MN(T)$, $M1(T)$, $M2(T)$ and $M3(T)$ at temperature T° K respectively as follows:

$$MN(T)/M1(T) = r_{N1}(T);\ MN(T)/M2(T) = r_{N2}(T);\ MN(T)/M3(T) = r_{N3}(T) \quad [2]$$

where $r_{N1}(T)$, $r_{N2}(T)$ and $r_{N3}(T)$ are constants and can be theoretically calculated from the blackbody Planck curves for any temperature T° K. Thus substituting T1, T2 and T3 for T in Equation [2], one has $r_{N1}(T1)$, $r_{N1}(T2)$, $r_{N1}(T3)$, $r_{N2}(T1)$, $r_{N2}(T2)$, $r_{N2}(T3)$, $r_{N3}(T1)$, $r_{N3}(T2)$ and $r_{N3}(T3)$ are all constants and can be calculated from the Planck blackbody curves like those illustrated in FIG. 1. For example, the ratio $r_{N1}$ is simply the value of $M_\lambda$ at $\lambda N$ (CWL of neutral filter) divided by the $M_\lambda$ value at $\lambda 1$ (CWL of absorption filter for gas G1). Thus substituting source temperatures T1, T2 and T3 for T in Equation [2], one has $r_{N1}(T1)$, $r_{N1}(T2)$, $r_{N1}(T3)$, $r_{N2}(T1)$, $r_{N2}(T2)$, $r_{N2}(T3)$, $r_{N3}(T1)$, $r_{N3}(T2)$ and $r_{N3}(T3)$ and they are all constants and can be calculated from the Planck blackbody curves for source temperatures T1, T2 and T3 respectively like those illustrated in FIG. 1.

For a given sample chamber design for the sensor, let the absorption of the gases G1, G2 and G3 be $\alpha$, $\beta$, and $\gamma$ respectively. Note that in general, the absorption $\alpha$, $\beta$ and $\gamma$ are very mildly dependent upon the gas temperature but is independent of the blackbody source temperatures T1, T2 or T3. Assuming that there are no scattering losses like in most gas detection or measurement scenarios, the respective transmittances $t_G$ for gases G1, G2 and G3 respectively are given as follows:

$$t_{G1}=1-\alpha;\ t_{G2}=1-\beta;\ t_{G3}=1-\gamma$$

Thus when gas species G1, G2 and G3 are absent in the sample chamber, $\alpha=\beta=\gamma=0$ and $t_{G1}=t_{G2}=t_{G3}=1$.

The detector output a, b and c respectively for the three optical channels when the 4-passband filter is in place at the detector can now be expressed as:

$$a = K(T1) + A[a_1 \times t_{G1} \times M1(T1) + a_2 \times t_{G2} \times M2(T1) + a_3 \times t_{G3} \times M3(T1)] \quad [3]$$

$$b = K(T2) + A[a_1 \times t_{G1} \times M1(T2) + a_2 \times t_{G2} \times M2(T2) + a_3 \times t_{G3} \times M3(T2)] \quad [4]$$

$$c = K(T3) + A[a_1 \times t_{G1} \times M1(T3) + a_2 \times t_{G2} \times M2(T3) + a_3 \times t_{G3} \times M3(T3)] \quad [5]$$

where:

$K(T1)$, $K(T2)$ and $K(T3)$ are constants, namely independent of $\alpha$, $\beta$, and $\gamma$ of the gases to be detected when $MN(Ti)$ [i=1,2,3] are known and are given as follows:

$$K(T1) = \in \times MN(T1) \times \eta(\lambda N) \times \Delta\lambda N \times \eta(OS) \times R \times G(COM)$$
$$= k \times MN(T1);$$

$$K(T2) = \in \times MN(T2) \times \eta(\lambda N) \times \Delta\lambda N \times \eta(OS) \times R \times G(COM)$$
$$= k \times MN(T2);$$

$$K(T3) = \in \times MN(T3) \times \eta(\lambda N) \times \Delta\lambda N \times \eta(OS) \times R \times G(COM)$$

$$A = \in \times \eta(OS) \times R \times G(COM);$$

$$a_1 = \eta(\lambda 1) \times \Delta\lambda 1$$

$$a_2 = \eta(\lambda 2) \times \Delta\lambda 2$$

$$a_3 = \eta(\lambda 3) \times \Delta\lambda 3$$

Using Equation [2] and substituting the various temperatures of T1, T2 and T3 for T, we have:

$$a = K(T1) + A \times MN(T1)[a_1 \times t_{G1}/r_{N1}(T1) + a_2 \times t_{G2}/r_{N2}(T1) + a_3 \times t_{G3}/r_{N3}(T1)] \quad [6]$$

$$b = K(T2) + A \times MN(T2)[a_1 \times t_{G1}/r_{N1}(T2) + a_2 \times t_{G2}/r_{N2}(T2) + a_3 \times t_{G3}/r_{N3}(T2)] \quad [7]$$

$$c = K(T3) + A \times MN(T3)[a_1 \times t_{G1}/r_{N1}(T3) + a_2 \times t_{G2}/r_{N2}(T3) + a_3 \times t_{G3}/r_{N3}(T3)] \quad [8]$$

Substituting the values of $K(T1)$, $K(T2)$ and $K(T3)$ into Equations [6], [7] and [8] above, we have:

$$a = MN(T1)[k + A \times [a_1 \times t_{G1}/r_{N1}(T1) + a_2 \times t_{G2}/r_{N2}(T1) + a_3 \times t_{G3}/r_{N3}(T1)]] \quad [9]$$

$$b = MN(T2)[k + A \times [a_1 \times t_{G1}/r_{N1}(T2) + a_2 \times t_{G2}/r_{N2}(T2) + a_3 \times t_{G3}/r_{N3}(T2)]] \quad [10]$$

$$c = MN(T3)[k + A \times [a_1 \times t_{G1}/r_{N1}(T3) + a_3 \times t_{G2}/r_{N2}(T3) + a_3 \times t_{G3}/r_{N3}(T3)]] \quad [11]$$

We have now successfully established the causality relationships between the outputs of the detector with all the relevant sensor parameters for the three optical channels related respectively to the three blackbody temperatures of the source as expressed in Equations [9], [10] and [11] above. The next step of our formulation is to define the necessary system phenomenological conditions for the sensor in order to permit the numerical evaluation of all the non-constant parameters in Equations [9], [10] and [11].

By flowing only nitrogen gas through the sample chamber and creating a situation where none of gas species G1, G2 nor G3 are present, we have $t_{G1} = t_{G2} = t_{G3} = 1.0$ and Equations [9], [10] and [11] can now be rewritten with new constants as follows:

$$a = MN(T1)[k + d1]; \text{ where } d1 = A \times [a_1/r_{N1}(T1) + a_2/r_{N2}(T1) + a_3/r_{N3}(T1)] \quad [12]$$

$$b = MN(T2)[k + d2]; \text{ where } d2 = A \times [a_1/r_{N1}(T2) + a_2/r_{N2}(T2) + a_3/r_{N3}(T2)] \quad [13]$$

$$c = MN(T3)[k + d3]; \text{ where } d3 = A \times [a_1/r_{N1}(T3) + a_2/r_{N2}(T3) + a_3/r_{N3}(T3)] \quad [14]$$

Note that k, d1, d2 and d3 are constants that can be calculated. By experimentally measuring the values of a, b and c, with only nitrogen in the sample chamber, one can determine the values of MN(T1), MN(T2) and MN(T3) by using Equations [12], [13] and [14] respectively as follows:

$$MN(T1) = a/(k + d1); MN(T2) = b/(k + d2); MN(T3) = c/(k + d3)$$

When the values of MN(T1), MN(T2) and MN(T3) are determined via the use of just nitrogen gas present in the sample chamber, Equations [9], [10] and [11] contain only the unknowns $t_{G1}, t_{G2}, t_{G3}$ and the measured detector outputs for the three optical channels, namely a, b and c. The rest of the parameters are system constants that can be a priori calculated. Thus by measuring the values of a, b and c in Equations [9], [10] and [11], the concentrations of the gas species G1, G2 and G3 can be determined simultaneously as expressed respectively by the value of $t_{G1}, t_{G2}$ and $t_{G3}$.

Finally, let us determine how to establish the individual calibration curves for gas species G1, G2 and G3. The calibration curve for G1 can be determined via Equation [9] with the use of only nitrogen gas ($t_{G1} = t_{G2} = t_{G3} = 1.0$ or $\alpha = \beta = \gamma = 0$) and a number of samples (e.g. 6) with known concentration of G1 gas. With $t_{G2} = t_{G3} = 1.0$, Equation [9] can be rewritten as:

$$a = m + n \times t_{G1} \text{ or } t_{G1} = (a - m)/n \quad [15]$$

where the constants m and n are given as:

$$m = MN(T1) \times k + A \times [a_2/r_{N2}(T1) + a_3/r_{N3}(T1)] \text{ and}$$

$$n = A \times a_1/r_{N1}(T1)$$

By using Equation [15], for a particular concentration of the G1 gas, we can determine the corresponding $t_{G1}$. In other words, we can now determine the concentration curve for the G1 gas as follows:

| G1 gas concentration (ppm) | $t_{G1}$ |
|---|---|
| 0 ppm | V1 |
| 200 ppm | V2 |
| 500 ppm | V3 |
| 1,000 ppm | V4 |
| 1,200 ppm | V5 |
| 1,500 ppm | V6 |
| 2,000 ppm | V7 |

By determining the set of "$V_i$" values (i=1 through 7) via putting into the sample chamber only nitrogen and known concentration of G1 gas, one can obtain the calibration curve for G1 since subsequently it is the $t_{G1}$ value that is being measured by the single beam NDIR gas sensor designed using the differential source temperature technique.

Similarly, the calibration curves for gas species G2 and G3 can also be determined. After such calibrations for all the three gases are inputted to the sensor, subsequent measured values of $t_{G1}, t_{G2}$ and $t_{G3}$ will provide simultaneously the to-be-determined concentration values for the gases species G1, G2 and G3 present in the sample chamber of the sensor.

Thus it has been described above the mathematical formulation of the present invention for a multiple differential source emission temperature technique encompassing, as an example, the simultaneous detection of three gases using a four-passband interference filter. Such a mathematical formulation is not limited to the simultaneous detection of only three gases. It works for the simultaneous detection of N gases with a custom "N+1"-passband filter. The limitation, however, lies in the state-of-the-art for the design and fabrication of these multi-passband filters. It is also limited by the spectral location of the gases to be detected, their spectral separation and also the availability of appropriate neutral reference bands to be used with such a technique.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept. For example, the present invention is especially well suited to development of a simple multi-channel NDIR gas sensor for detecting both water vapor and carbon dioxide, and such a sensor would be especially well suited to HVAC and IAQ applications and represents a tremendous potential advance in the field, not to mention the possibility of tremendous energy savings from use of a such a sensor having a much lower cost than sensors presently available for use in such situations. In this regard, it would be especially desirable to construct such a sensor using a custom 3-passband filter encompassing the absorption band of CO2 at 4.26 microns, the absorption band of water vapor at 2.60 microns and a neutral reference band at 3.91 microns, and two appropriate driving temperatures for the infrared source.

Accordingly, it will be apparent to those skilled in the art that still further changes and modifications in the actual concepts described herein can readily be made without departing from the spirit and scope of the disclosed inventions as defined by the following claims.

What is claimed is:

1. A method for detecting the concentrations of N gas species from a single beam NDIR gas sensor having a differential infrared source and a (N+1)-passband filter mounted at a single infrared detector, comprising the steps of:
- (1) driving the infrared source with N input power levels so as to render said source into emitting at N distinct temperatures whose radiation outputs are characterized by N corresponding Planck curves which are dependent only upon the respective source temperatures and which link a Spectral Radiant Emittance MsubLamba with wavelength;
- (2) measuring N detector outputs at the single infrared detector; and
- (3) detecting the concentrations of N different gas species, each of the N gas species having its own unique infrared absorption passband, by (a) setting up N causality relationship equations linking outputs of the detector respectively for N different source temperatures and a set of relevant parameters of the sensor components, (b) determining the values of all of the parameters for the N equations utilizing appropriate boundary conditions except the N concentrations for the respective N gas species, and (c) solving for the N gas concentrations with the measured N detector outputs, there being N equations and N unknowns;
- wherein a neutral passband and N absorption passbands for N gases are incorporated into the (N+1)-passband filter; and
- wherein N is an integer of 2 or more.

2. The method of claim 1, wherein the infrared source is a non-genuine blackbody source.

3. The method of claim 2, wherein the infrared source is a genuine blackbody source uniquely characterized by just one single source temperature that emits radiation in all wavelengths long and short dependent upon its operating temperature.

4. The method of claim 1, wherein each of the N absorption passbands for N gases is specific to passing a particular spectral radiation for one of the N gases to be detected.

5. The method of claim 1, wherein steps (3)(a) and (3)(b) are performed as part of an initialization process.

6. The method of claim 5, wherein step (3)(c) is repeated along with steps (1) and (2) to repeatedly determine the N gas concentrations of the N gas species.

7. The method of claim 1, comprising the further step in step (3) of using N calibration curves to detect the concentrations of N different gas species.

8. A method for detecting the concentrations of N gas species from a single beam NDIR gas sensor having a differential infrared source and a multiple-passband filter mounted at a single infrared detector wherein a neutral passband and N absorption passbands for N gases species are incorporated into the multiple-passband filter, each of the N gas species having its own unique infrared absorption passband, comprising the steps of:
- (1) setting up N causality relationship equations linking outputs of the detector respectively for N different source temperatures and a set of relevant parameters of the sensor components;
- (2) determining the values of all of the parameters for the N equations utilizing appropriate boundary conditions except the N concentrations for the respective N gas species;
- (3) driving the infrared source with N input power levels so as to render said source into emitting at N distinct temperatures whose radiation outputs are characterized by N corresponding Planck curves which are dependent only upon the respective source temperatures and which link a Spectral Radiant Emittance MsubLamba with wavelength;
- (4) measuring N detector outputs at the single infrared detector; and
- (5) detecting the concentrations of N different gas species by solving the N causality relationship equations for the N gas concentrations with the measured N detector outputs, there being N equations and N unknowns, wherein N is an integer of 2 or more.

9. A single beam NDIR gas sensor for detecting the concentrations of N gas species, comprising:
- a differential infrared source;
- a single infrared detector
- a multiple-passband filter mounted at the single infrared detector, said multiple-passband filter having a neutral passband and N absorption passbands for N gases species incorporated into the multiple-passband filter, each of the N gas species having its own unique infrared absorption passband;
- a driver for the infrared source with N input power levels so as to render said source into emitting at N distinct temperatures whose radiation outputs are characterized by N corresponding Planck curves which are dependent only upon the respective source temperatures and which link a Spectral Radiant Emittance MsubLamba with wavelength; and
- electronics for detecting the concentrations of N different gas species by solving N causality relationship equations with N unknowns linking outputs of the detector respectively for N different source temperatures and a set of relevant parameters of the sensor components that have been determined utilizing appropriate boundary conditions except the N concentrations for the respective N gas species, wherein N is an integer of 2 or more.

10. The sensor of claim 9, wherein the infrared source is a non-genuine blackbody source.

11. The sensor of claim 2, wherein the infrared source is a genuine blackbody source uniquely characterized by just one single source temperature that emits radiation in all wavelengths long and short dependent upon its operating temperature.

* * * * *